US006645725B2

(12) United States Patent
Yeaman (10) Patent No.: US 6,645,725 B2
(45) Date of Patent: Nov. 11, 2003

(54) DIAGNOSTIC ASSAY FOR ENDOMETRIOSIS (75) Inventor: Grant R. Yeaman, Etna, NH (US)

(73) Assignee: Research Corporation Technologies, Inc., Tucson, AZ (US)

(*) Notice: Subject to any disclaimer, the term of this patent is extended or adjusted under 35 U.S.C. 154(b) by 0 days.

(21) Appl. No.: 09/837,964

(22) Filed: Apr. 19, 2001

(65) Prior Publication Data
US 2001/0046713 A1 Nov. 29, 2001

Related U.S. Application Data
(60) Provisional application No. 60/198,881, filed on Apr. 19, 2000.

(51) Int. Cl.$^7$ ............................................... G01N 33/53

(52) U.S. Cl. ..................... 435/7.1; 435/7.42; 435/7.93; 435/7.94; 436/501; 436/518

(58) Field of Search ................................. 435/69.3, 7.1, 435/7.72, 7.93; 436/504, 538, 540, 813

(56) References Cited

U.S. PATENT DOCUMENTS

| | | | |
|---|---|---|---|
| 4,241,044 A | * 12/1980 | Kim et al. ................. | 436/518 |
| 4,968,604 A | 11/1990 | Beatty | |
| 5,110,911 A | 5/1992 | Samuel et al. | |
| 5,242,799 A | * 9/1993 | Samuel et al. ............... | 435/7.1 |
| 5,342,759 A | 8/1994 | Litman et al. | |
| 5,455,332 A | * 10/1995 | Turner et al. ............ | 530/387.7 |
| 5,512,659 A | 4/1996 | Ullman et al. | |
| 5,529,898 A | 6/1996 | Rogers et al. | |
| 5,561,049 A | 10/1996 | Vold et al. | |
| 5,716,778 A | 2/1998 | Weng et al. | |
| 5,846,740 A | 12/1998 | Tobin et al. | |
| 5,976,810 A | 11/1999 | Wagatsuma et al. | |

OTHER PUBLICATIONS

Brinton, D. et al., "Endometriosis: Identification by Carbonic Anhydrase Autoantibodies and Clinical Features", *Annals of Clinical and Laboratory Science*, vol. 26, No. 5, pp. 406–420 (1996).
Burns, W. et al., "Pathophysiology of Endometriosis–Associated Infertility", *Clinical Obstetrics and Gynecology*, vol. 42, No. 3, pp. 586–610 (1999).
Metcalfe, S. et al., "A New Indicator of Human Malignant Tumour", *Br. J. Cancer*, vol. 49, pp. 337–342 (1984).
Longenecker, B.M. et al., "Monoclonal Antibodies and Synthetic Tumor–Associated Glycoconjugates in the Study of the Expression of Thomsen–Friedenreich–Like and Tn–Like Antigens on Human Cancers", *JNCI*, vol. 78, No. 3, pp. 489–496 (1987).

Longenecker, B.M. et al., "Monoclonal Antibody Against a Cryptic Carbohydrate Antigen of Murine and Human Lymphocytes. I. Antigen Expression in Non–Cryptic or Unsubstituted Form on Certain Murine Lymphomas, on a Spontaneous Murine Mammary Carcinoma, and on Several Human Adenocarcinomas", *Int. J. Cancer*, vol. 33, pp. 123–129 (1984).
Hanisch, F–G. et al., "Monoclonal Antibody BW835 Defines a Site–specific Thomsen–Friedenreich Disaccharide Linked to Threonine within the VTSA Motif of MUC1 Tandem Repeats", *Cancer Research*, vol. 55, pp. 4036–4040 (1995).
Karsten, U. et al., "A New Monoclonal Antibody (A78–G/A7) to the Thomsen–Friedenreich Pan–Tumor Antigen", *Hybridoma*, vol. 14, No. 1, pp. 37–44 (1995).
Kiechle, F. et al., "Carbonic Anhydrase Antibody in Sera from Patients with Endometriosis", *Immunopathology*, vol. 101, No. 5, pp. 611–615 (1994).
Dahlenborg, K. et al., "Human Monoclonal Antibodies Specific for the Tumour Assoicated Thomsen–Friedenreich Antigen", *Int. J. Cancer*, vol. 70, pp. 63–71 (1997).
D'Cruz, O. et al., "Antibodies to Carbonic Anhydrase in Endometriosis: Prevalence, Specificity, and Relationship to Clinical and Laboratory Parameters", *Fertility and Sterility*, vol. 66, No. 4, pp. 547–556 (1996).
Hanisch, F–G. et al., "The Thomsen–Friedenreich (TF) Antigen: A Critical Review on the Structural, Biosynthetic and Histochemical Aspects of a Pancarcinoma–Associated Antigen", *Histol Histopathol*, vol. 12, pp. 263–281 (1997).
Ishikawa, E. et al., "Development of Ultrasensitive Enzyme Immunoassay Reviewed with Emphasis on Factors which Limit the Sensitivity", *Molecular and Cellular Probes*, vol. 5, pp. 81–95 (1991).
Stein, R. et al., "Human Lung Carcinoma Monoclonal Antibody Specific for the Thomsen–Friedenreich Antigen", *Cancer Research*, vol. 49, pp. 32–37 (1989).
Ravn–Skovlund, V., "ABH and Related Histo–Blook Group Antigens in Normal & Malignant Human Endometrium in Relation to Genetic and Hormonal Factors", *APMIS Suppl. 69*, vol. 105, pp. 5–33 (1997).
Sakamoto, Y. et al., "Expression of Thomsen–Friedenreich Antigen (T–Ag) in Gynecologic Cancer Tissues", *Acta Orst Gynaec Jpn*, vol. 39, No. 11, pp. 1980–1986 (1987).

(List continued on next page.)

Primary Examiner—Long V. Le
Assistant Examiner—Gary W. Counts
(74) Attorney, Agent, or Firm—Scully, Scott, Murphy & Presser (57) ABSTRACT The present invention provides a method for detecting endometriosis in a patient and is an improvement over invasive and expensive surgical procedures. The method employs immunoassays which detect autoantibodies in a serum sample which react with Thomsen-Friedenreich antigen (Tf). Increased levels of autoantibodies in a serum sample from the patient which bind to Tf-like antigen is indicative of endometriosis in the patient.

18 Claims, 4 Drawing Sheets

OTHER PUBLICATIONS

Ravn–Skovlund, V. et al., "Thomsen–Friedenreich–Related Antigen in Human Endometrium: An Immunohistochemical Study Employing the Monoclonal Antibody 49H.8.", *APMIS*, vol. 96, pp. 552–558 (1988).

Rahman, A.F. et al., "A Monoclonal Antibody Specific for the Thomsen–Friedenreich Cryptic T Antigen", *The Journal of Immunology*, vol. 129, No. 5, pp. 2021–2024 (1982).

Moncayo, H. et al., "Ovarian Failure and Autoimmunity: Detection of Autoanibodies Directed Against Both the Unoccupied Luteinizing Hormone/Human Chorionic Gonadotropin Receptor and the Hormone–Receptor Complex of Bovine Corpus Luteum", *J. Clin. Invest*, vol. 84, pp. 1857–1865 (1989).

Rier, S. et al., "Immune Aspects of Endometriosis: Relevance of the Uterine Mucosal Immune System", *Seminars in Reproductive Endocrinology*, vol. 15, No. 3, pp. 209–220 (1997).

Yasui, T. et al., "Clinical Implications of Serum Antibody to Thomsen–Friedenreich Antigen in Patients with Gynecological Malignancies", *Acta Obst Gynaec Jpn*, vol. 40, No. 5, pp. 583–587 (1988).

Witz, C., "Current Concepts in the Pathogenesis of Endometriosis", *Clinical Obstetrics and Gynecology*, vol. 42, No. 3, pp. 566–585 (1999).

Wild, D. et al., "The Immunoassay Handbook", pp. 49–82.

* cited by examiner

DIAGNOSTIC ASSAY FOR ENDOMETRIOSIS

CROSS REFERENCE TO RELATED APPLICATION

This application claims priority from U.S. Provisional Application No. 60/198,881, filed on Apr. 19, 2000.

BACKGROUND OF THE INVENTION

Endometriosis is a common disorder characterized by the growth of endometrial cells at extrauterine (ectopic) sites. It is a common disease which may affect up to 10% of reproductive age women (1). Although the etiology of endometriosis remains enigmatic, altered cellular and humoral immune function is clearly a feature of established disease (2–4).

Autoantibodies to endometrial antigens and deposition of complement components have been described in a number of studies (reviewed in 2) and a number of serum, peritoneal fluid and endometrial antigens have been described. Perhaps the best characterized tissue antigens described, thus far, are the human chorionic gonadotropin receptor (5) and isoforms I and II of the enzyme carbonic anhydrase 6–8. Antibodies to transferrin and α2-Heremans Schmidt glycoprotein ($\alpha_2$-HSG) have also been described and proposed as diagnostic markers 9, 10. While considerable work has been carried out in terms of measuring the incidence of these antibodies in endometriosis, reproductive diseases, and other autoimmune diseases, the nature of the epitopes involved has received scant attention. The identified antigens are all glycoproteins. With only one apparent exception (5), carbohydrate antigens on these proteins have not been evaluated.

In accordance with the present invention, it has been surprisingly found that a common carbohydrate moiety is present on the different aforementioned endometrial antigens. The common carbohydrate moiety is the Thomsen-Friedenreich related antigen, Galβ1-3GalNAc, also referred to as Tf antigen or Tf-like antigen. As used herein, Tf-like antigen also encompasses Tf antigen. Tf antigen is a cryptic disaccharide structure masked by sialic acid. The sialic acid moieties may be removed by sialidases such as neuraminidase. Tf antigen is present on human erythrocytes and is a tumor-associated antigen in epithelial tissues.

The present invention provides diagnostic methods based on autoantibody reactivity with Tf-like antigen. The diagnostic methods are helpful in determining the presence of endometriosis in a patient and are an improvement over the current invasive methods of diagnosis.

SUMMARY OF THE INVENTION

The present invention provides methods for diagnosing endometriosis in a patient. In one embodiment of the invention, a method for diagnosing endometriosis in a patient comprises the steps of
 (a) obtaining a serum sample from said patient,
 (b) incubating Thomsen-Friedenreich (Tf)-like antigen with said serum sample,
 (c) detecting autoantibody reactivity with the Tf-like antigen in said sample, and;
 (d) correlating an increased level of autoantibody reactivity to the Tf-like antigen in the serum sample with a diagnosis of endometriosis in said patient.

Antibody reactivity may be determined by immunoassays such as immunometric or competitive assays.

In one embodiment of the invention, an immunometric assay comprises the steps of:

(a) immobilizing Tf-like antigen on a solid support,
 (b) adding an aliquot of serum sample from a patient to the Tf-like antigen bound on the solid support and incubating,
 (c) adding a labeled anti-human immunoglobulin to the solid support wherein said anti-human immunoglobulin is part of a signal producing system,
 (d) separating free labeled antibody from bound antibody,
 (e) measuring the signal generated by the solution containing the solid support and;
 (f) correlating an increase in signal strength with a diagnosis of endometriosis in the patient.

In another embodiment of the invention, a competitive immunoassay comprises the steps of:
 (a) preparing a reaction mixture by incubating a constant amount of a labeled antibody which is bound to Tf-like antigen with different concentrations of a serum sample from a patient wherein said labeled antibody is part of a signal producing system,
 (b) separating bound labeled antibodies from free autoantibodies,
 (c) measuring the signal generated by the labeled antibody in the reaction mixture and;
 (d) correlating a decrease in signal strength after addition of the serum sample from a patient with a diagnosis of endometriosis in the patient.

In another embodiment of the invention, a competitive immunoassay comprises the steps of:
 (a) preparing a reaction mixture by incubating a first antibody which is bound to Tf-like antigen with different concentrations of a serum sample from a patient,
 (b) adding a constant amount of a second antibody to the reaction mixture wherein said second antibody recognizes a constant region of the heavy chain of the first antibody and wherein the second antibody is labeled and part of a signal producing system,
 (c) separating free labeled second antibody from bound antibody,
 (d) measuring the signal generated by the second antibody in the reaction mixture; and
 (e) correlating a decreased level of signal strength with a diagnosis of endometriosis in the patient.

In those cases where the antibody is enzyme labeled, the additional steps of adding a substrate to the solid support which reacts with the enzyme-labeled antibody followed by incubation are performed prior to measuring the generated signal.

BRIEF DESCRIPTION OF THE DRAWINGS

FIG. 4 is a western blot of a gel run with partially purified fraction of $\alpha_2$-HSG and probed with endometriosis sera HRP goat anti-human IgG antibody which demonstrates that deglycosylation of $\alpha_2$-HSG abolishes autoantibody binding. Neuraminidase was used to cleave terminal sialic acid (lanes B, E, H). Complete removal of carbohydrate was then achieved using EndoF/PNG'ase digestion (lanes C, F, H). Removal of sialic acid and all carbohydrate was confirmed by reduction in molecular weight as shown by reactivity with goat anti-$\alpha_2$-HSG (lane A-C). Lanes A, D, and G were untreated. Removal of terminal sialic acid with neuraminidase reduced reactivity with patient serum (lane D versus E). The remaining reactivity in this fraction was at the same molecular weight as the undigested $\alpha_2$-HSG, indicating that the autoantibody binding is dependent on the presence of terminal sialic acid. Complete removal of carbohydrate by neuraminidase treatment followed by EndoF/PNG'ase digestion completely abolished reactivity (lane F). No equivalent reactivity was observed using pooled male control sera (lanes G–I).

DETAILED DESCRIPTION OF THE INVENTION

The present invention provides diagnostic methods for detecting endometriosis in a patient. The diagnostic methods are based on immunoassays which detect the presence of autoantibodies in a patient's serum reacting with Thomsen-Friedenreich (Tf) antigen, including Tf-like antigen. As used herein, Tf-like antigen also encompasses Tf antigen. Increased levels of autoantibodies in a serum sample which bind Tf-like antigen, when compared to normal serum levels of autoantibodies which bind Tf-like antigen, correlate with a diagnosis of endometriosis in the patient.

A blood sample may be conveniently drawn from a patient by venipuncture or other suitable means. A serum sample may be prepared from the blood sample using well known methods.

There are many different types of immunoassays which may be used in the methods of the present invention. Any of the well known immunoassays may be adapted to detect the level of autoantibodies in a serum sample which react with the Tf-like antigen, such as e.g., enzyme linked immunoabsorbent assay (ELISA), fluorescent immunosorbent assay (FIA), chemical linked immunosorbent assay (CLIA), radioimmuno assay (RIA), and immunoblotting. For a review of the different immunoassays which may be used, see: *The Immunoassay Handbook*, David Wild, ed., Stockton Press, New York, 1994. Preferably, a competitive immunoassay with solid phase separation or an immunometric assay for antibody testing is used. See, *The Immunoassay Handbook*, chapter 2.

In a typical assay, the reagents include a serum sample from a patient, the autoantibodies to be detected (contained in the serum sample), Tf-like antigen, and means for producing a detectable signal.

Thus, in one embodiment of the invention, the method for diagnosing endometriosis in a patient employs an immunometric assay for antibody testing. In this embodiment, the Tf-like antigen is immobilized on a solid support or surface such as a bead, plate, slide or microtiter dish. An aliquot of serum sample from a patient is added to the solid support and allowed to incubate with the Tf-like antigen in a liquid phase. An antibody that recognizes a constant region in human autoantibodies present in the serum which have reacted with the Tf-like antigen is added. This antibody is an anti-human immunoglobulin and is also part of a signal producing system. Anti-human immunoglobulin which is specific for IgA, IgG, or IgM heavy chain constant regions may be employed. After separating the solid support from the liquid phase, the support phase is examined for a detectable signal. The presence of the signal on the solid support indicates that autoantibodies to Tf-like antigen present in the serum sample have bound to the Tf-like antigen on the solid support.

The signal producing system is made up of one or more components, at least one of which is a label, which generate a detectable signal that relates to the amount of bound and/or unbound label i.e., the amount of label bound or unbound to the Tf-like antigen. The label is a molecule that produces or which may be induced to produce a signal. Examples of labels include fluorescers, enzymes, chemiluminescers, photosensitizers or suspendable particles. The signal is detected and may be measured by detecting enzyme activity, luminescence or light absorbance. Radiolabels may also be used and levels of radioactivity detected and measured using a scintillation counter.

Examples of enzymes which may be used to label the anti-human immunoglobulin include β-D-galactosidase, horseradish peroxidase, alkaline phosphatase, and glucose-6-phosphate dehydrogenase ("G6PDH"). Examples of fluorescers which may be used to label the anti-human immunoglobulin include fluorescein, isothiocyanate, rhodamine compounds, phycoerythrin, phycocyanin, allophycocyanin, o-phthaldehyde and fluorescamine. Chemiluminescers include e.g., isoluminol.

Free labeled antibody is separated from bound antibody and if necessary, an appropriate substrate with which the label, e.g., enzyme, reacts is added and allowed to incubate.

In a preferred embodiment, the anti-human immunoglobulin is enzyme labeled with either horseradish peroxidase or alkaline phosphatase.

The amount of color, fluorescence, luminescence, or radioactivity present in the reaction (depending on the signal producing system used) is proportionate to the amount of autoantibodies in a patient's serum which react with the Tf-like antigen. Quantification of optical density may be performed using spectrophotometric methods. Quantification of radiolabel signal may be performed using scintillation counting.

Increased levels of autoantibodies reacting with Tf-like antigen over normal serum levels correlate with a diagnosis of endometriosis in the patient.

In another embodiment of the invention, the method for diagnosing endometriosis in a patient employs a competitive immunoassay where a known antibody and a patient's autoantibodies compete for binding to Tf. In this embodiment, a constant amount of a labeled antibody which is known to bind to Tf-like antigen is incubated with different concentrations of a serum sample from a patient. For example, the mouse monoclonal antibody 49H.8, (Rahman and Longenecker, 1982, J. Immun. 129(5): 2021–4) known to bind to Tf, may be used. Other monoclonal antibodies which bind to Tf-like antigen and which may be used as antibody in the competitive immunoassay include 155H7 and 170H82 (Longenecker et al. 1987, J. Nat. Cancer Inst., 78(3): 489–96, A78-G/A7 (Karsten et al. 1995, Hybridoma 14(1): 37–44), HB-T1 (DAKO Co.), RS1-114 and AHB-25B (Stein et al. 1989, Cancer Res. 49(1): 32–7), HT8 (Metcalfe et al., 1984, Br. J. Cancer 49(3): 337–42), 161H4 (Longenecker et al., 1987), HH8 (Clausen et al. 1988), and BW835 (Hanish et al, 1995, Cancer Res. 55(18): 4036–40). As described above, the antibody may be labeled with a fluorescer, enzyme, chemiluminescer, photosensitizer, suspendable particles, or radioisotope. Preferably, the known antibody is enzyme labeled. After incubation, bound labeled antibodies are separated from free autoantibodies. Depending on the signal producing system used and if necessary, an appropriate substrate with which the labeled antibody reacts is added and allowed to incubate. The signal generated by the sample is then measured. A decrease in optical density or radioactivity from before and after addition of the serum sample or between experimental and control samples, is indicative that autoantibodies in the serum sample have bound to Tf. Decreased optical density or radiolabeled signal when compared to experimental serum samples from normal patients, correlates with a diagnosis of endometriosis in a patient.

In a preferred embodiment of the competitive immunoassay, an indirect method using two antibodies is used. The first antibody is a Tf-like antigen specific antibody as described in the preceding paragraph with the exception that it is not labeled. The first antibody is incubated with different concentrations of a serum sample from a patient. A constant amount of a second antibody is then added to the sample. The second antibody recognizes constant regions of the heavy chains of the first antibody. For example, the second antibody may be an antibody which recognizes constant regions of the heavy chains of mouse immunoglobulin which has reacted with the Tf-like antigen (anti-mouse immunoglobulin). The second antibody is labeled with a fluorophore, chemilophore or radioisotope, as described above. Free labeled second antibody is separated from bound antibody. If an enzyme-labeled antibody is used, an appropriate substrate with which the enzyme label reacts is added and allowed to incubate. A decrease in optical density or radioactivity from before and after addition of the serum sample or between experimental and control samples is indicative that autoantibodies in the serum sample have bound to Tf. Decreased optical density or radioactivity when compared to experimental serum samples from normal patients correlates with a diagnosis of endometriosis in a patient.

Enzymes may be covalently linked to Tf-like antigen reactive antibodies for use in the methods of the invention using well known methods. There are many well known conjugation methods. For example, alkaline phosphatase and horseradish peroxidase may be conjugated to antibodies using glutaraldehyde. Horseradish peroxidase may also be conjugated using the periodate method. Commercial kits for enzyme conjugating antibodies are widely available. Enzyme conjugated anti-human and anti-mouse immunoglobulin specific antibodies are available from multiple commercial sources.

Biotin labeled antibodies may be used as an alternative to enzyme linked antibodies. In such cases, bound antibody would be detected using commercially available streptavidin-horseradish peroxidase detection systems.

Enzyme labeled antibodies produce different signal sources, depending on the substrate. Signal generation involves the addition of substrate to the reaction mixture. Common peroxidase substrates include ABTS®(2,2'-azinobis(ethylbenzothiazoline-6-sulfonate)), OPD (O-phenylenediamine) and TMB (3,3', 5,5'-tetramethylbenzidine). These substrates require the presence of hydrogen peroxide. p-nitrophenyl phospate is a commonly used alkaline phosphatase substrate. During an incubation period, the enzyme gradually converts a proportion of the substrate to its end product. At the end of the incubation period, a stopping reagent is added which stops enzyme activity. Signal strength is determined by measuring optical density, usually via spectrophotometer.

Alkaline phosphatase labeled antibodies may also be measured by fluorometry. Thus in the immunoassays of the present invention, the substrate 4-methylumbelliferyl phosphate (4-UMP) may be used. Alkaline phosphatase dephosphorylated 4-UMP to form 4-methylumbelliferone (4-MU), the fluorophore. Incident light is at 365 nm and emitted light is at 448 nm.

For use in the methods of the present invention, Tf-like antigen may be obtained from various sources. For example, Tf-like antigen may be purified from conditioned culture medium used to cultivate tumor cell lines such as the adenocarcinoma cell line LS174T, obtainable through the American Type Culture Collection (ATCC). Transitional cell carcinoma lines may also serve as source of Tf-like antigen. Tf-like antigen may be purified from such conditioned culture medium by affinity chromatograpy using an MAb 49H.8-CnBr activated Sepharose column. Gel filtration may also be performed for additional purification. Still further purification of Tf-like antigen may be achieved by utilizing lectin affinity chromatography with insolubilized peanut agglutinin (PNA) or other lectin. PNA may be obtained from E-Y Laboratories, San Mateo, Calif.

Purified serum proteins bearing Tf-like antigens such as IgA, hemopexin, and alpha-2-Heremans Schmidt may also be used as antigens. A preferred source of Tf-like antigen is commercially synthesized Tf-like antigens covalently linked to bovine serum albumin. Tf-like antigen and its glycoforms are available from commercial vendors such as BioCarb as recently described by Dahlenborg et al. (1997) *In. J. Cancer* 70:63–71. Alternatively, Tf-like antigens may be obtained by custom synthesis from commercial vendors. Monoclonal antibodies which react with Tf-like antigen are readily available.

MAb49.H (isotype IgM) may be prepared and purified as reported by Rahman et al., (1982) *J. Immunol.* 129:2021–2024 and Longenecker et al. (1984) *Int. J. Cancer* 33:123–129. The disclosure of these articles and other articles cited in this application are incorporated herein as if fully set forth.

In order to practice the methods of the present invention, the relevant immunoassay must be standardized. Since Tf-like antigen is usually associated with a glycoprotein, it is naturally heterogenous. The source of such heterogeneity may include sialylation. To this end, an ampoule of an international standard (IS) or international reference preparation (IRP) should be obtained. The National Institute for Biological Standards and Control (NIBSC, Blanche Lane, South Mimms, Potters Bar, Herts EN63QG) may prepare such a sample of Tf-like antigen and assign an international unit (IU). Multiple sets of secondary standards, from which future lots of calibrators may be assigned values, should also be prepared.

The immunoassays of the present invention require the use of calibrators in order to assign values or concentrations to unknown samples. Typically, a set of about six calibrators is run prior to the unknown samples from which a calibration curve is plotted. The concentrations of the unknown samples are determined by interpolation. Interpolation is best carried out by a computer program. For a discussion on calibration, see *The Immunoassay Handbook*, chapter 2.

The present invention also provides therapies for reducing, preventing and/or ameliorating endometriosis in a patient. In this embodiment of the invention, purified antibodies which bind Tf-like antigen are injected into a patient.

The following examples further illustrate the invention.

EXAMPLE 1

Materials and Methods
Preparation of Tissue Homogenate

Fresh ectopic and eutopic endometrium, peritoneal fluid, and serum were obtained from hysterectomy patients with the informed consent of the patients. Fresh tissue (1–2 grams) was added to 10 ml ice-cold PBS containing Complete Protease Inhibitor Cocktailä (Boehringer Mannheim, Indianapolis, Ind.) and maintained at 4° C. throughout the preparation. The tissue was homogenized for 1 minute with a Polytron homogenizer (Brinkman, Lucerne, Switzerland) followed by centrifugation at 13000 g for 10 minutes. The supernatant was collected and sonicated using a Branson 250 sonifier (Danbury, Conn.). The tissue homogenate was 0.22 mm filtered and stored at 20° C.

Preparation of Serum

Peripheral venous blood (60 ml) was drawn from healthy volunteers into glass vacutainer tubes (no additive) and allowed to clot for 4 hours at room temperature. Serum was then removed to sterile tubes and delipidated by centrifugation at 12000 g for 30 minutes at 4° C.

Purification of Tissue Autoantigens

Following homogenization, tissue antigens were passed through a Protein G FPLC column (Amersham Pharmacia, Piscataway, N.J.) to remove IgG. Proteins not retained by the protein G column were then applied to an anion exchange column (MonoQ FPLC, Amersham Pharmacia, Piscataway, N.J.) following equilibration in 50 mM sodium phosphate pH 8.0. Bound proteins were eluted from the column using a linear 0–0.5 M NaCl gradient in the same buffer, followed by a step gradient to 1 M NaCl also in the same buffer. All proteins of interest eluted prior to the 1 M NaCl gradient.

Purification of Serum Autoantigens $\alpha_2$-HSG was purified from normal whole human serum by anion exchange chromatography as described for the tissue antigens above using a HiPrep 16/10 Q XL column. This partially purified $\alpha_2$-HSG was used in some experiments as indicated in the test. Further purification was carried out on a second anion exchange column (Mono Q) equilibrated with 20 mM piperazine buffer pH 5.0 and eluted in the same buffer using a NaCl gradient as described above. A final homogeneous preparation of $\alpha_2$-HSG was obtained following gel filtration on an FPLC Superose 12 column (Amersham Pharmacia, Piscataway, N.J.). $\alpha_2$-HSG concentrations were monitored by ELISA.

IgA1 was purified from whole serum by anion exchange chromatography and jacalin agarose affinity chromatography as previously described (11).

Transferrin and Hemopexin were purified from whole serum by metal chelate chromatography on a column packed with Chelating Sepharose Fast Flow (Amersham Pharmacia, Piscataway, N.J.) charged with $Zn^{2+}$ ions. The column and serum were pre-equilibrated in 20 mM sodium phosphate buffer containing 150 mM NaCl. Zinc binding proteins were eluted using a linear 0–0.5 M imidazole gradient in the same buffer. The resulting transferrin and hemopexin-containing fractions (as determined by western blot analysis) were separately pooled and further purified on a mono Q anion exchange column at pH 8.0 as already described. This protocol resulted in an electrophoretically pure hemopexin preparation. Transferrin was not however resolved from hemopexin in the transferrin preparation.

Modification of Carbohydrate-epitopes on Glycoproteins

Terminal sialic acid moieties were removed from glycoproteins by treatment with agarose-conjugated neuraminidase. One milligram of protein in 0.5 ml was incubated with 5 Units of neuraminidase (Sigma, St Louis, Mo.) in 50 mM sodium acetate, 150 mM sodium chloride, 4 mM calcium chloride, pH 5.5 overnight at 37° C. Agarose beads were removed by centrifugation at 4000 g for 5 minutes. Supernatants were removed and stored at 4° C.

Core carbohydrate groups were removed from glycoproteins by treatment with endoglycosidase F (Endo F) and peptide-N-glycosidase F (PNG'ase F). This was obtained as a commercial kit from Glyko (Novato, Calif.). Forty micrograms of neuraminidase-treated protein were denatured by heating to 100° C. for 2 minutes in the presence of 20 mM sodium phosphate pH 7.5, 50 mM EDTA, 0.1% v/v SDS, 0.5% b-mercaptoethanol. To avoid inhibition of PNG'ase F by SDS, 0.1% Tween-20 was added to the denatured sample after cooling. The denatured protein was then incubated with 667 deglycosylation Units (DGU) of the Endo F/PNG'ase F mix at 37° C. for 18 hours.

Removal of jacalin-reactive glycoproteins from samples was achieved by pre-adsorption with an excess of jacalin-conjugated agarose beads (Vector, Burlingame, Calif.). Samples were incubated with jacalin-conjugated agarose for 30 minutes at room temperature before centrifugation at 4000 g for 5 minutes. Supernatants were removed and stored at 4° C.

Antibodies and Glycoproteins

Immunoglobulin-fractions of sheep anti-human $\alpha_2$-HSG and sheep anti-human transferrin were obtained from Biodesign International (Kennebunk, Me.). Goat anti-human hemopexin antiserum was obtained from Kent Laboratories (Redmond, Wash.). HRP-conjugated rabbit anti-sheep IgG and HRP-conjugated rabbit anti-goat IgG were both from Jackson Immunoresearch Laboratories (West Grove, Pa.). HRP-conjugated goat-anti human IgA (a-chain specific) and HRP-conjugated goat-anti human IgG (g-chain specific) were purchased from (Sigma). Commercial $\alpha_2$-HSG was obtained from Calbiochem-Novabiochem (La Jolla, Calif.).

SDS-PAGE

SDS-PAGE was performed according to the method of Laemmli (12). Briefly, equal volumes of 2× gel loading buffer were added to protein samples and boiled for 5 minutes. Where appropriate, proteins were resolved under reducing conditions (5% v/v b-mercaptoethanol in gel loading buffer). Re-association of reduced proteins was prevented by adding iodoacetamide (final concentration 60 mM) to samples after boiling. Protein samples were resolved using 4% –15% gradient gels (Biorad, Hercules, CA). For direct visualization of proteins, gels were placed in 0.02% v/v SYPRO-Orange (Biorad, Hercules, Calif.) in 7.5% v/v acetic acid for 30 minutes. Gels were then rinsed in 7.5% acetic acid and viewed on a gel imager (Alpha Innotech Corporation, San Leandro, Calif.).

Immunoblotting

Proteins were transferred to nitrocellulose membranes from SDS-gels using a Biorad Transblot SD semi-dry blotter. Ponceau Red staining confirmed transfer of proteins to nitrocellulose membranes. Membranes were blocked overnight at 4° C. in 5% w/v fat-free powdered milk, 0.5% Tween-20 in PBS. Primary antibody or serum was added to blocking solution then incubated for 2 hours at room temperature. Membranes were then washed 6 times for 5 minutes per wash in PBS. The HRP-conjugated secondary antibodies were diluted in 3% w/v fat-free milk powder with 0.05% v/v Tween-20 in PBS. Membranes were incubated for 2 hours at room temperature before washing 6 times for 5 minutes as described. Proteins were then detected by enhanced chemiluminescence (ECL) (Amersham Pharmacia, Piscataway, N.J.). Where appropriate, nitrocellulose membranes were stripped and re-probed by washing twice for 5 minutes per wash in 0.9% w/v NaCl before agitation in 100 mM Glycine-HCl pH 1.5 for 30 minutes at room temperature. Membranes were then washed 3 times for 5 minutes per wash with PBS pH 7.4. The membranes were blocked and probed with antibodies as described.

Enzyme Linked Immunosorbent Assay (ELISA).

Wells of Falcon Microtest III microtitre plates (Becton Dickinson, Oxnard, Calif.) were coated overnight at 4° C. with 10 µl protein diluted to 100 µl in sodium carbonate buffer pH9.2. Plates were then washed 3 times in PBS containing 0.05% v/v Tween-20. Wells were blocked with 3% w/v BSA in PBS / Tween-20 (blocking buffer) for 1 hour at 37° C. before washing 3 times. Primary antibody or test serum was diluted in blocking buffer as appropriate and 100 µl added to each well. Plates were incubated for 2 hours at 37° C. and washed 3 times in PBS / Tween-20. HRP-conjugated secondary antibody was diluted in blocking buffer and 100 µl added to each well. Plates were then washed 3 times. 100 ml of the calorimetric HRP-substrate, ABTS was added to each well and incubated for 30 minutes at room temperature. Plates were read at 405 nm with a Dynatech plate reader (Chantilly, Va.) Data was analyzed using Graphpad Prism software.

EXAMPLE 2

Figure 1:
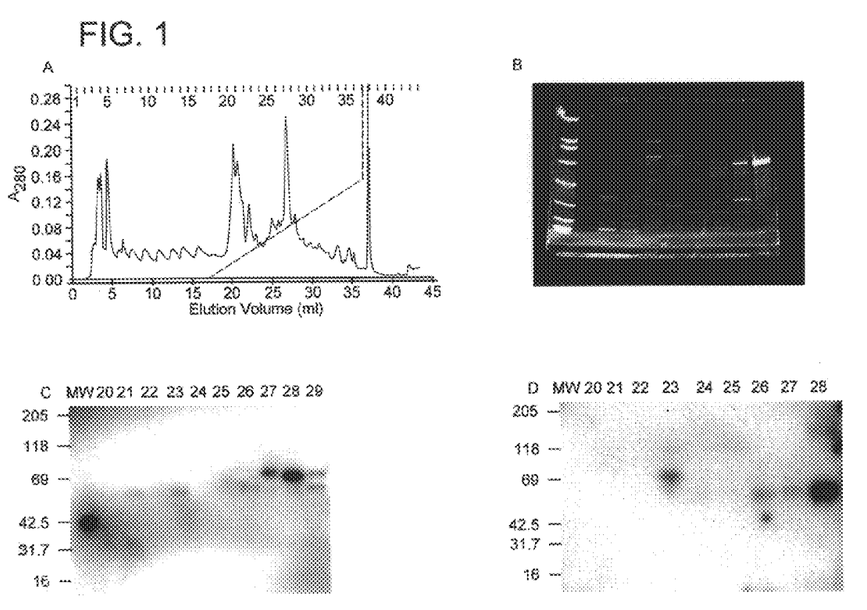
FIG. 1a is an elution profile showing MonoQ anion exchange chromatography of homogenized eutopic endometrium from an endometriosis patient. The homogenate was passed through a protein G column to remove IgG prior to loading on the MonoQ column. Initial peaks prior to the start of the salt gradient represent multiple 1 ml homogenate loads. Elution conditions: 50 mM Tris/HCl pH 8.0. Elution was in the same buffer with a linear 0–0.5 NaCl gradient (stepped to 1 M NaCl) and is denoted by the dashed line. Fractions corresponding to the gel loading (FIGS. 1b–d) are indicated along the top of the graph.
FIG. 1b shows a 5–15% gradient gel of selected column fractions indicated in FIG. 1a run under reducing conditions and stained with SYPRO Orange.
FIG. 1c is an autoradiograph displaying proteins in the homogenate fractions recognized by IgG present in pooled endometriosis serum. Stripping and reprobing of the same blot using pooled normal male serum showed no reactivity with the same bands. IgG binding activity was detected in fraction 24 using control sera but similar binding was not seen with endometriosis sera. The 45.2 kDa molecular weight marker carbonic anhydrase II shows reactivity. This same reactivity was not observed with the control sera.
FIG. 1d is an autoradiograph showing IgA binding activity of the endometriosis sera. Probing of the blot with anti-IgA a-chain specific antibody in the absence of a primary serum showed that IgA was present in these fractions.

Identification of Autoantigens in Ectopic Endometrium, Eutopic Endometrium, Peritoneal Fluid and Sera Soluble endometrial protein preparations were prepared from hysterectomy tissue as described in the materials and methods, and subjected to protein G chromatography to remove IgG. The resulting IgG-free preparations were then subjected to anion exchange chromatography (FIG. 1a). Fractions from this column were then analyzed by SDS-PAGE under reducing conditions (FIG. 1b). Protein bands on identical gels were transferred to nitrocellulose for western blot analysis. Development of the western blots was carried out using sera from both pooled endometriosis patients and pooled normal male donors as primary antibody sources. FIG. 1c shows a typical example of the antigens identified in a proliferative phase eutopic endometrium from a patient (W1345). Autoreactive IgG was restricted to the endometriosis patient sera (FIG. 1c) as compared to the same blots probed with a control serum from a normal male donor (not shown).

IgG g-chain binding was detected against fraction 24 of the mono Q column with the control serum but not in other fractions (not shown). Interestingly, a similar reactivity against fraction 24 was not present in blots developed using the endometriosis serum. The molecular weight of the reactive proteins detected using pooled endometriosis sera correlate well with those described by other workers 6, 10. A total of 10 autoreactive bands were detected on a western blot probed with pooled endometriosis sera. A 72 kDa band was detected in fraction 23 with both IgA α-chain specific and IgG γ-chain specific second antibodies (FIGS. 1c and 1d). This band was initially identified as transferrin on the basis of its molecular weight and the NaCl concentration at which it eluted from the MonoQ column (the elution of transferrin at this position was confirmed by western blot analysis using a sheep anti-transferrin antibody, not shown). A 54 kDa protein was also detected in this fraction with the IgG γ-chain specific antibody but not the anti-IgA α-chain specific antibody. This protein elutes in a position identical to partially desialylated $\alpha_2$-HSG (data not shown). $\alpha_2$-HSG has previously been identified as an autoantigen in endometriosis patients (10). The IgG reactive band of 59 kDa observed in fractions 26 and 29 is the α-chain of IgA and the elution positions correspond to the known elution positions, under these run conditions, of monomeric and dimeric IgA respectively. The identity of this protein as IgA α-chain was confirmed by stripping and reprobing the blot with an anti α-chain specific antibody (not shown). This blot also showed the presence of anti-α-chain reactive bands in fraction 23 (the transferrin containing fraction). The presence of IgA antigens in this fraction most likely arises from IgA covalently complexed with other serum proteins 13, 14.

Fraction 26 also contained a reactive band at 72 kDa and fraction 28 and 29 had bands at 69 kDa. These later bands showed no activity on the α-chain specific blot. The presence of an IgG antibody in endometriosis patients which recognizes the α-chain of IgA was confirmed by western blot using highly purified serum IgA1 (see FIG. 7). In contrast, no IgA autoantibodies against endometrial antigens other than in those fractions, which contain IgA α-chain, were observed.

Figure 2:
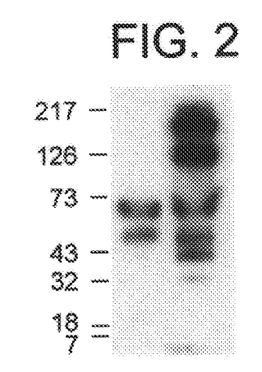
FIG. 2 is a western blot of peritoneal fluid (W1517) run out on a 5–15% SDS-PAGE gel under reduced and alkylated conditions. The western blot was then incubated with either sheep anti-human $\alpha_2$-HSG followed by HRP-goat anti-sheep (lane a) or with a 1:100 dilution of endometriosis sera followed by HRP-goat IgG g-chain specific antibody (1:1000 dilution). Clearly visible are $\alpha_2$-HSG in lane a and bands of equivalent molecular weight in lane b.

An ovarian ectopic endometrial sample from the same patient (w1345) had autoantigenic proteins of molecular weights 54, 47, 43, and 34 KDa (not shown). The 54 kDa protein was $\alpha_2$-HSG as determined by a western blot developed with a sheep anti-$\alpha_2$-HSG specific antibody. $\alpha_2$-HSG was also detected in peritoneal lavage fluid from a different patient (W1517) by western blot. In addition to the 54 kDa antigen, antigens of 186, 126, 68, 43, 37, and 34 kDa were present in the peritoneal fluid (FIG. 2). Reactivity with two molecular weight markers was observed with both pooled patients and individual sera (see FIG. 1c and FIG. 3). These markers were myosin at 205 kD and carbonic anhydrase II at 42 kD. Reactivity with the myosin band was also seen with both the pooled male control sera and some individual male sera. In contrast, reactivity with anhydrase II was specific to the endometriosis sera and this protein has been reported by other workers as an autoantigen in endometriosis 7, 8.

In summary, autoantigens in preparations from eutopic and ectopic endometrium and peritoneal lavage have been identified. In agreement with previously published reports, $\alpha_2$-HSG, transferrin and carbonic anhydrase II are autoantigens recognized by sera from endometriosis patients. In addition, results presented here also demonstrate that the α-chain of IgA is also an autoantigen recognized by the same sera. Since these proteins show no significant homology at the protein level, it is unlikely that a common peptide epitope is shared by all four proteins. Three of the four proteins, $\alpha_2$-HSG, α-chain of IgAl and possibly carbonic anhydrase II, do however, share a common carbohydrate epitope. This O-linked carbohydrate structure contains a Galβ1-3NAcGal epitope which is recognized by the jackfruit (Artocarpus integrifolia) lectin jacalin. The results presented here confirm previous reports that $\alpha_2$-HSG and carbonic anhydrase are among the autoantigens recognized by autoantibodies present in endometriosis sera. The present study extends these results to show that IgA1 and hemopexin are also autoantigens recognized by sera from endometriosis patients.

EXAMPLE 3
Jacalin Preadsorption Removes Autoantibody Binding $\alpha_2$-Heremans Schmidt glycoprotein ($\alpha_2$-HSG) was chosen as a model antigen to investigate a potential role for jacalin reactive carbohydrates in the endometriosis autoantibody response. Initial experiments using $\alpha_2$-HSG purchased from commercial sources proved to be unsatisfactory. This was because of the variability of glycoforms present in these preparations. In common with most sialated glycoproteins, $\alpha_2$-HSG loses terminal sialic acid residues during storage. Fully sialated $\alpha_2$-HSG from normal human serum was freshly prepared. In order to avoid biasing the preparation with respect to its carbohydrate content, lectin based affinity purification protocols were avoided and instead a combination of anion exchange and gel filtration chromatography was used. A three step procedure of anion exchange on a MonoQ column at pH 8.0, followed by a second MonoQ column at pH 5.0, and a final gel filtration step on a superose 12 column, resulted in the purification of the fully sialated glycoform of $\alpha_2$-HSG with a molecular weight of 58 kDa.

Figure 3:
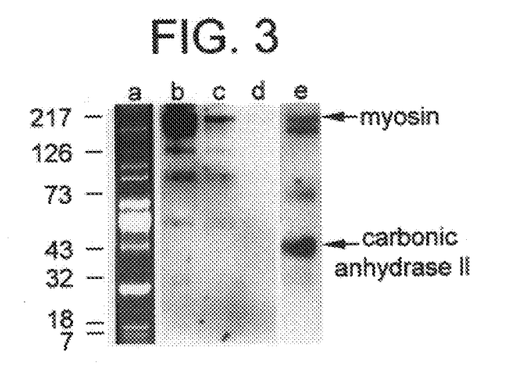
FIG. 3a is an SDS-PAGE gel showing a partially purified fraction of $\alpha_2$-HSG (MonoQ column, pH 8.0). Fourteen protein bands are visible after staining with SYPRO Orange.
FIG. 3b is a western blot of a gel run with partially purified fraction of $\alpha_2$-HSG and probed with endometriosis sera HRP goat anti-human IgG antibody. Five protein bands were detected.
FIG. 3c is a western blot as described in FIG. 3b except that the protein fraction was treated with neuraminidase prior to electrophoresis. Antibody binding to all of the proteins is clearly reduced.
FIG. 3d is a western blot as described for FIG. 3b except that the $\alpha_2$-HSG fraction was subjected to preadsorption with jacalin agarose prior to electrophoresis. All antibody binding is removed.
FIG. 3e shows autoreactivity with myosin and carbonic anhydrase II in the molecular weight markers.

When experiments were carried out using a partially purified $\alpha_2$-HSG fraction from the first anion exchange column, autoreactivity with endometriosis serum on western blot was abolished following pre-incubation with jacalin agarose (FIG. 3). Fourteen protein bands were observed on SYPRO orange stained SDS-PAGE gels (FIG. 3 lane a). Reactivity with endometriosis sera was observed with 5 proteins (FIG. 3 lane b). The reactive proteins had approximate molecular weights of 230, 188, 168, 120, and 58 kDa; the 58 kDa being $\alpha_2$-HSG. Binding by IgG in endometriosis sera of all of these 5 bands was abolished following incubation with jacalin agarose (FIG. 3 lane d), indicating that the binding of the autoantibodies was to all of the jacalin binding proteins present in the fraction and not just to $\alpha_2$-HSG. Protein staining of gels of pre- and post-absorbed fraction 13 show that the removal of activity was not caused by a non-specific removal of proteins in the fraction. The protein concentrations of adsorbed and unadsorbed were adjusted such that total protein loading on the gels used for western blotting was uniform.

The carbohydrate structure recognized by jacalin is very specific and binding is dependent on the presence of the Tf. Jacalin recognizes the disaccharide Galβ1-3GalNAc, which is present within some O-linked oligosaccharides. Galβ1-3GalNAc is expressed by a very limited number of the many plasma proteins. These proteins include IgA1, IgD, C1-inhibitor, hemopexin, plasminogen, α1-antitrypsin, α2-macroglubulin, 8S-α3 glycoprotein, chorionic gonadotropin (hCG) and $\alpha_2$-HSG (15). With regard to hCG, it is of interest that the receptor for hCG expresses also expresses Tf-like antigen and that autoantibodies found in infertile patients both with and without concomitant endometriosis bind to the receptor 5.

EXAMPLE 4
Removal of Carbohydrate Abolishes Autoantibody Binding

Figure 4:
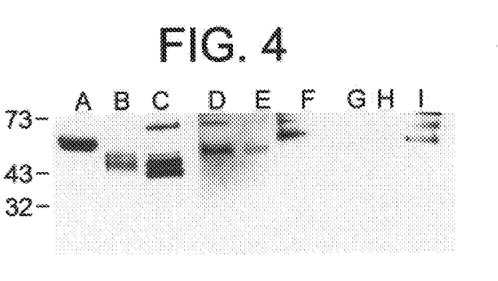

Removal of proteins recognized by the autoantibodies by jacalin does not in itself determine whether a common carbohydrate epitope(s) is involved. To determine whether the carbohydrate is essential for the recognition of $\alpha_2$-HSG by the endometriosis autoantibodies, reactivity with deglycosylated $\alpha_2$-HSG was investigated. $\alpha_2$-HSG carbohydrate was removed in a two step procedure. First, neuraminidase was used to cleave terminal sialic acid. Second, complete removal of carbohydrate was then achieved using a further EndoF/PNG'ase digestion step. Untreated, neuraminidase treated, and deglycosylated $\alpha_2$-HSG were then subjected to western blot analysis at equal protein loads (FIG. 4). Removal of sialic acid and all carbohydrate was confirmed by reduction in molecular weight as shown by reactivity with sheep anti-$\alpha_2$-HSG (FIG. 4 lanes A–C).

The sheep anti-$\alpha_2$-HSG antibody is reactive with the peptide and shows no reactivity with other jacalin binding proteins on double immunodiffusion (data not shown). Removal of terminal sialic acid with neuraminidase reduced reactivity with patient serum (FIG. 4 lanes D and E). The remaining reactivity in this fraction was at the same molecular weight as the undigested $\alpha_2$-HSG, indicating that the autoantibody binding is dependent on the presence of terminal sialic acid. Complete removal of carbohydrate by neuraminidase treatment followed by EndoF/PNG'ase digestion completely abolished reactivity (FIG. 4 lane F). This reduction in autoantibody binding following neuraminidase was not restricted to $\alpha_2$-HSG since similar treatment of the partially purified $\alpha_2$-HSG fraction resulted in reduced binding to all 5 reactive proteins (FIG. 3 lane c).

TABLE 1

Correlation of Identified Endometriosis Antigens and Jacalin Binding Activity

| Antigen | Endometriosis Antigen In this Study/ (published study) | Jacalin Reactivity In this study/ (published reactivity) |
|---|---|---|
| α-HSG | Yes/[9,10] | Yes/[63] |
| Carbonic anhydrase I/II | Yes/[6–8] | no/unknown |
| Hemopexin | Yes/no | Yes/[15,40] |
| IgA | Yes/no | Yes/multiple reviewed in[15] |
| CD23 | No/soluble form elevated[53–55] | No/acts as a Gal-GalNac lectin like jacalin[64,65] |
| hCG Receptor | No/[5] | No/[66] |

These results show that (with the exception of transferrin) a common carbohydrate epitope is recognized on $\alpha_2$-HSG, carbonic anhydrase, hemopexin and the a-chain of IgA1 (see table 1 for a summary of antigens identified in this, and published studies, and their jacalin reactivity). This conclusion was reached on the basis that all of the identified antigens (with the exception of transferrin and carbonic anhydrase II) are known to bind the lectin jacalin, and that the removal of carbohydrate from the antigens removed the ability of endometriosis sera to bind these antigens.

EXAMPLE 5
Binding of Autoantibody to Bovine Fetuin

Figure 5:
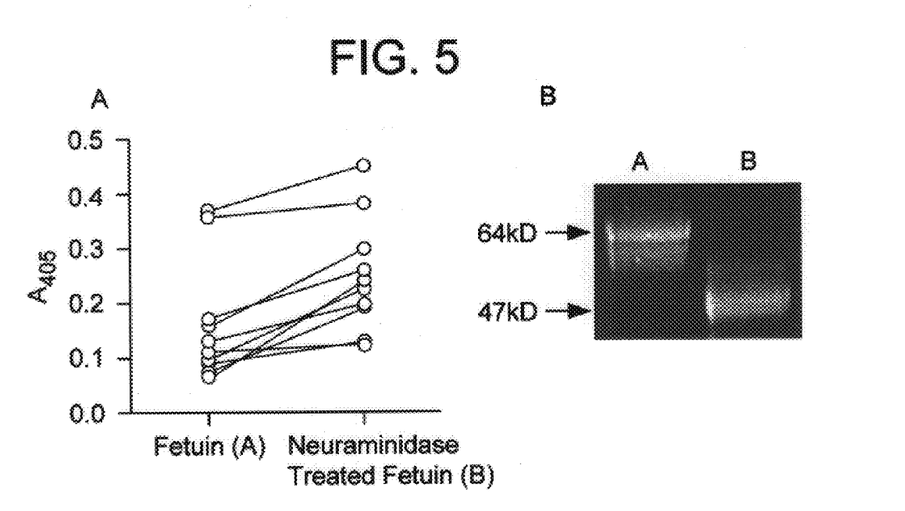
FIG. 5a demonstrates that desialylation of bovine fetuin increases reactivity with endometriosis sera. As measured by ELISA, a slight but significant increase in binding is seen following treatment with neuraminidase.
FIG. 5b is a SYPRO Orange stained gel showing the molecular weight reduction in fetuin following neuraminidase treatment. Lane A is untreated; lane B is neuraminidase treated.

Bovine fetuin, the homologue of human $\alpha_2$-HSG, bears the same jacalin binding carbohydrate moiety as human $\alpha_2$-HSG. Sheep antiserum raised against human SG peptide does not show cross-reactivity with bovine fetuin, suggesting significant differences in antigenicity between the two species despite considerable sequence homology. Sera from endometriosis patients show positive reactivity by ELISA and western blot with bovine fetuin (FIG. 5.). Neuraminidase treatment of fetuin, in contrast to -HSG, slightly increased autoantibody reactivity on ELISA (FIG. 5). However, more complete desialylation, or complete deglycosylation of bovine fetuin abolished antibody binding, giving additional evidence that the autoantibody response in endometriosis patients is carbohydrate dependent (not shown). The increase in binding to fetuin following incomplete neuraminidase treatment may result from bovine fetuin being more heavily sialated than its human counterpart.

EXAMPLE 6
D-Galactose Dependency of Autoantibody Binding

Jacalin binding is dependent on the presence of a Galβ1-3NacGal moiety. If the autoantibody response involves this epitope, binding should be competitively inhibited by D-galactose, as is the case for jacalin binding. Binding of endometriosis IgG to $\alpha_2$-HSG on western blots was completely abolished in the presence of 0.8M D-Galactose, indicating that D-Galactose may form a part of the epitope recognized by the autoantibodies (not shown).

Figure 6:
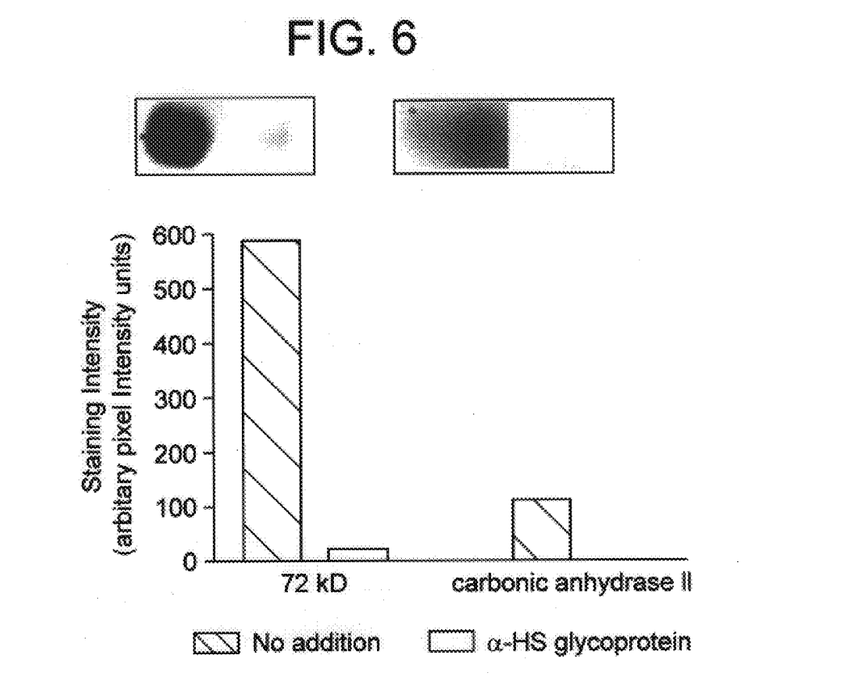
FIG. 6 both graphically and by radioautography depicts that binding to the 72 kDa antigen and,carbonic anhydrase II is inhibited in the presence of $\alpha_2$-HSG.

EXAMPLE 7
Serum Autoantigens Recognized by Endometriosis Serum Share a Common Epitope Since a common carbohydrate epitope accounts for the autoreactivity with the different antigens identified above, then autoantibody binding should be blocked in the presence of an excess of a different antigen. This proved to be the case: addition of a 10 fold excess of highly purified $\alpha_2$-HSG or bovine fetuin both inhibited binding of autoantibody to carbonic anhydrase II and the 72 kDa antigen (FIG. 6).

Figure 7:
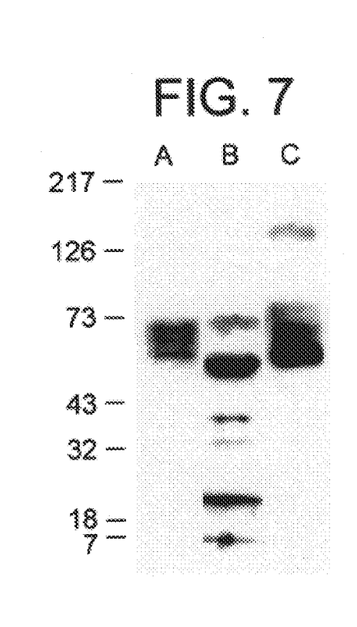
FIG. 7 is a western blot analysis of purified proteins following transfer to nitrocellulose from 5–15% gradient gels run reduced and alkylated. Purified hemopexin (lane A), $\alpha_2$-HSG (lane B), and serum IgA1 (lane C) are autoantigens recognized by IgG antibodies in endometriosis sera.

Is hemopexin, rather than transferring, the 72 kDa autoantigen in endometriosis? Of the antigens described thus far, all, with the exception of transferrin, express the O-linked carbohydrates recognized by jacalin. No such carbohydrate structures are expressed on transferrin, and jacalin does not bind to transferrin 15. This leaves three possibilities: either an anti-transferrin response distinct from the jacalin carbohydrate response is present in endometriosis sera, or the reactivity which purifies with transferrin is against a contaminant in the transferrin preparations, or both. Two reactive proteins of ~70 kDa were found in the anion exchange fractions of eutopic endometrium W1345. One eluted early in the salt gradient in the same fraction as transferrin. The other protein eluted at higher salt concentration in the same fractions as IgA. Examination of the Swiss 2D database indicates that jacalin-binding proteins of similar molecular weight and isoelectric point include hemopexin. When hemopexin was purified by $Zn^{2+}$ metal chelate chromatography and anion exchange chromatography, a homogeneous preparation was obtained. Identity was confirmed by western blotting of fractions with a hemopexin specific antibody. When tested against endometriosis patient serum this protein was recognized as an autoantigen (FIG. 7). Western blot analysis of the same protein with an antibody specific for transferrin showed no reactivity with the purified hemopexin. When fractions from the same column were investigated for the transferrin reactivity, an earlier peak from the anion exchange column was found to contain transferrin. Western blot analysis of the transferrin-containing fractions with anti-hemopexin revealed the presence of hemopexin with similar mobility to transferrin on SDS-PAGE. Double immunodiffusion showed no lines of identity when anti-hemopexin and anti-transferrin were precipitated against the peak transferrin fraction, indicating that the antisera were antigen specific (not shown). The presence of jacalin binding activity in this transferrin preparation was confirmed by the presence of a precipitin line in double immunodiffusion against jacalin (not shown). Further experiments are currently underway to determine the nature of the antigen which co-purifies with transferrin, but it is of interest that the 72 kDa binding activity was inhibited by the addition of a pure $\alpha_2$-HSG preparation (FIG. 6).

1. Wheeler J. M. (1992) Epidemiology and prevalence of endometriosis. *Infert Reprod Med Clin North Am*, 3, 345.
2. Burns W. N. & Schenken R. S. (1999) Pathophysiology of endometriosis-associated infertility. *Clin Obstet Gynecol*, 42, 586.
3. Witz C. A. (1999) Current concepts in the pathogenesis of endometriosis. *Clin Obstet Gynecol*, 42, 566.
4. Rier S. E. & Yeaman G. R. (1997) Immune aspects of endometriosis: relevance of the uterine mucosal immune system. *Semin Reprod Endocrinol*, 15, 209.
5. Moncayo H., Moncayo R., Benz R., Wolf A. & Lauritzen C. (1989) Ovarian failure and autoimmunity. Detection of autoantibodies directed against both the unoccupied luteinizing hormone/human chorionic gonadotropin receptor and the hormone-receptor complex of bovine corpus luteum. *Journal of Clinical Investigation*, 84, 1857.
6. Brinton D. A., Quattrociocchi-Longe T. M. & Kiechle F. L. (1996) Endometriosis: identification by carbonic anhydrase autoantibodies and clinical features. *Ann Clin Lab Sci*, 26, 409.
7. D'Cruz O. J., Wild R. A., Haas G. G., Jr. & Reichlin M. (1996) Antibodies to carbonic anhydrase in endometriosis: prevalence, specificity, and relationship to clinical and laboratory parameters. *Fertil Steril*, 66, 547.

8. Kiechle F. L., Quattrociocchi-Longe T. M. & Brinton D. A. (1994) Carbonic anhydrase antibody in sera from patients with endometriosis. *Am J Clin Pathol,* 101, 611.
9. Mathur S. P., Holt V. L., Lee J. H., Jiang H. & Rust P. F. (1998) Levels of antibodies to transferrin and alpha 2-HS glycoprotein in women with and without endometriosis. *Am J Reprod Immunol,* 40, 69.
10. Pillai S., Zhou G. X., Arnaud P., Jiang H., Butler W. J. & Zhang H. (1996) Antibodies to endometrial transferrin and alpha 2-Heremans Schmidt (HS) glycoprotein in patients with endometriosis [published erratum appears in *Am J Reprod Immunol* 1997 Mar;37(3):277]. *Am J Reprod Immunol,* 35, 483.
11. Yeaman G. R. & Kerr M. A. (1987) Opsonization of yeast by human serum IgA anti-mannan antibodies and phagocytosis by human polymorphonuclear leucocytes. *Clin Exp Immunol,* 68, 200.
12. Laemmli U. K. (1970) Cleavage of structural proteins during the assembly of the head of bacteriophage T4. *Nature,* 227, 680.
13. Struthers G. R., Lewin I. V. & Stanworth D. R. (1989) IgA-alpha 1 antitrypsin complexes in ankylosing spondylitis. *Ann Rheum Dis,* 48, 30.
14. Roberts-Thomson P. J. & Shepherd K. (1990) Molecular size heterogeneity of immunoglobulins in health and disease. *Clin Exp Immunol,* 79, 328.
15. Kabir S. (1998) Jacalin: a jackfruit (*Artocarpus heterophyllus*) seed-derived lectin of versatile applications in immunobiological research. *J Immunol Methods,* 212, 193.
16. Cao Y., Stosiek P., Springer G. F. & Karsten U. (1996) Thomsen-Friedenreich-related carbohydrate antigens in normal adult human tissues: a systematic and comparative study. *Histochem Cell Biol,* 106, 197.
17. Do S. I. & Cummings R. D. (1992) Presence of O-linked oligosaccharide on a threonine residue in 'the human transferrin receptor. *Glycobiology,* 2, 345.
18. Blasco E., Barra A., Nicolas M., Lecron J. C., Wijdenes J. & Preud'homme J. L. (1995) Proliferative response of human CD4+T lymphocytes stimulated by the lectin jacalin. *Eur i Immunol,* 25, 2010.
19. Keenan J. A., Chen T. T., Chadwell N. L., Torry D. S. & Caudle M. R. (1995) IL-1 beta, TNF-alpha, and IL-2 in peritoneal fluid and macrophage-conditioned media of women with endometriosis. *Am J Reprod Immunol,* 34, 381.
20. Awadalla S. G., Friedman C. I., Haq A. U., Roh S. I., Chin N. W. & Kim M. H. (1987) Local peritoneal factors: their role in infertility associated with endometriosis. *Am J Obstet Gynecol,* 157, 1207.
21. Mori H., Sawairi M., Nakagawa M., Itoh N., Wada K. & Tamaya T. (1992) Expression of interleukin-1 (IL-1) beta messenger ribonucleic acid (mRNA) and IL-1 receptor antagonist mRNA in peritoneal macrophages from patients with endometriosis. *Fertil Steril,* 57, 535.
22. Taketani Y., Kuo T. M. & Mizuno M. (1992) Comparison of cytokine levels and embryo toxicity in peritoneal fluid in infertile women with untreated or treated endometriosis. *Am J Obstet Gynecol,* 167, 265.
23. Fakih H., Baggett B., Holtz G., Tsang K. Y., Lee J. C. & Williamson H. O. (1987) Interleukin-1: a possible role in the infertility associated with endometriosis. *Fertil Steril,* 47, 213.
24. Hill J. A. & Anderson D. J. (1989) Lymphocyte activity in the presence of peritoneal fluid from fertile women and infertile women with and without endometriosis. *Am J Obstet Gynecol,* 161, 861.
25. Koyama N., Matsuura K. & Okamura H. (1993) Cytokines in the peritoneal fluid of patients with endometriosis. *Int J Gynaecol Obstet,* 43, 45.
26. Overton C., Fernandez-Shaw S., Hicks B., Barlow D. & Starkey P. (1996) Peritoneal fluid cytokines and the relationship with endometriosis and pain. *Hum Reprod,* 11, 380.
27. Harada T., Yoshioka H., Yoshida S., Iwabe T., Onohara Y., Tanikawa M. & Terakawa N. (1997) Increased interleukin-6 levels in peritoneal fluid of infertile patients with active endometriosis. *Am J Obstet Gynecol,* 176, 593.
28. Rier S. E., Zarmakoupis P. N., Hu X. & Becker J. L. (1995) Dysregulation of interleukin-6 responses in ectopic endometrial stromal cells: correlation with decreased soluble receptor levels in peritoneal fluid of women with endometriosis. *J Clin Endocrinol Metab,* 80, 1431.
29. Rier S. E., Parsons A. K. & Becker J. L. (1994) Altered interleukin-6 production by peritoneal leukocytes from patients with endometriosis. *Fertil Steril,* 61, 294.
30. Buyalos R. P., Funari V. A., Azziz R., Watson J. M. & Martinez-Maza O. (1992) Elevated interleukin-6 levels in peritoneal fluid of patients with pelvic pathology. *Fertil Steril,* 58, 302.
31. Rana N., Braun D. P., House R., Gebel H., Rotman C. & Dmowski W. P. (1996) Basal and stimulated secretion of cytokines by peritoneal macrophages in women with endometriosis. *Fertil Steril,* 65, 925.
32. Eisermann J., Gast M. J., Pineda J., Odem R. R. & Collins J. L. (1988) Tumor necrosis factor in peritoneal fluid of women undergoing laparoscopic surgery. *Fertil Steril,* 50, 573.
33. Halme J. (1989) Release of tumor necrosis factor-alpha by human peritoneal macrophages in vivo and in vitro. *Am J Obstet Gynecol,* 161, 1718.
34. Kabir S. & Wigzell H. (1989) A novel urinary sialoglycoprotein as the inhibitor of interleukin-1. *Clin Exp Immunol,* 77, 89.
35. Lebreton J. P., Joisel F., Raoult J. P., Lannuzel B., Rogez J. P. & Humbert G. (1979) Serum concentration of human alpha 2 HS glycoprotein during the inflammatory process: evidence that alpha 2 HS glycoprotein is a negative acute-phase reactant. *J Clin Invest,* 64, 1118.
36. Akhoundi C., Amiot M., Auberger P., Le Cam A. & Rossi B. (1994) Insulin and interleukin-1 differentially regulate pp63, an acute phase phosphoprotein in hepatoma cell line. *J Biol Chem,* 269, 15925.
37. Demetriou M., Binkert C., Sukhu B., Tenenbaum H. C. & Dennis J. W. (1996) Fetuin/alpha2-HS glycoprotein is a transforming growth factor-beta type II receptor mimic and cytokine antagonist. *J Biol Chem,* 271, 12755.
38. Bruner K. L., Eisenberg E., Gorstein F. & Osteen K. G. (1999) Progesterone and transforming growth factor-beta coordinately regulate suppression of endometrial matrix metalloproteinases in a model of experimental endometriosis [In Process Citation]. *Steroids,* 64, 648.
39. Kupker W., Schultze-Mosgau A. & Diedrich K. (1998) Paracrine changes in the peritoneal environment of women with endometriosis. *Hum Reprod Update,* 4, 719.
40. Pilatte Y., Rostoker G., Violleau K., Basta M. & Hammer C. H. (1995) Further identification of human plasma glycoproteins interacting with the galactose-specific lectin Jacalin. *J Chromatogr B Biomed Appl,* 668, 1.
41. Massova I., Kotra L. P., Fridman R. & Mobashery S. (1998) Matrix metalloproteinases: structures, evolution, and diversification. *Faseb J,* 12, 1075.

42. Solomon J. C., Stoll M. S., Penfold P., Abbott W. M., Childs R. A., Hanfland P. & Feizi T. (1991) Studies of the binding specificity of the soluble 14,000-dalton bovine heart muscle lectin using immobilised glycolipids and neoglycolipids. *Carbohydr Res*, 213, 293.

43. Ahmed H., Allen H. J., Sharma A. & Matta K. L. (1990) Human splenic galaptin: carbohydrate-binding specificity and characterization of the combining site. *Biochemistry*, 29, 5315.

44. Barondes S. H., Cooper D. N., Gitt M. A. & Leffler H. (1994) Galectins. Structure and function of a large family of animal lectins. *Journal of Biological Chemistry*, 269, 20807.

45. Kopitz J., von Reitzenstein C., Burchert M., Cantz M. & Gabius H. J. (1998) Galectin-1 is a major receptor for ganglioside GM1, a product of the growth-controlling activity of a cell surface ganglioside sialidase, on human neuroblastoma cells in culture. *Journal of Biological Chemistry*, 273, 11205.

46. Ochieng J., Green B., Evans S., James O. & Warfield P. (1998) Modulation of the biological functions. of galectin-3 by matrix metalloproteinases. *Biochimica et Biophysica Acta*, 1379, 97.

47. Ochieng J., Fridman R., Nangia-Makker P., Kleiner D. E., Liotta L. A., Stetler-Stevenson W. G. & Raz A. (1994) Galectin-3 is a novel substrate for human matrix metalloproteinases-2 and -9. *Biochemistry*, 33, 14109.

48. Bruner K. L., Matrisian L. M., Rodgers W. H., Gorstein F. & Osteen K. G. (1997) Suppression of matrix metalloproteinases inhibits establishment of ectopic lesions by human endometrium in nude mice. *J Clin Invest*, 99, 2851.

49. Choe Y. S., Shim C., Choi D., Lee C. S., Lee K. K. & Kim K. (1997) Expression of galectin-1 mRNA in the mouse uterus is under the control of ovarian steroids during blastocyst implantation. *Molecular Reproduction & Development*, 48, 261.

50. Van den Brule F. A., Fernandez P. L., Buicu C., Liu F. T., Jackers P., Lambotte R. & Castronovo V. (1997) Differential expression of galectin-1 and galectin-3 during first trimester human embryogenesis. *Developmental Dynamics*, 209, 399.

51. Phillips B., Knisley K., Weitlauf K. D., Dorsett J., Lee V. & Weitlauf H. (1996) Differential expression of two beta-galactoside-binding lectins in the reproductive tracts of pregnant mice. *Biology of Reproduction*, 55, 548.

52. Byrjalsen I., Larsen P. M., Fey S. J. & Christiansen C. (1995) Human endometrial proteins with cyclic changes in the expression during the normal menstrual cycle: characterization by protein sequence analysis. *Hum Reprod*, 10, 2760.

53. Odukoya O. A., Bansal A., Wilson A. P., Weetman A. P. & Cooke I. D. (1995) Serum-soluble CD23 in patients with endometriosis and the effect of treatment with danazol and leuprolide acetate depot injection. *Hum Reprod*, 10, 942.

54. Odukoya O., Bansal A. & Cooke I. (1996) Serum endometrial IgG antibodies and soluble CD23 concentrations in patients with endometriosis. *Acta Obstet Gynecol Scand*, 75, 927.

55. Odukoya O. A., Bansal A., Wilson P., Lim K., Weetman A. P. & Cooke I. D. (1996) Soluble CD23 protein in the peritoneal fluid of patients with endometriosis. *Hum Reprod*, 11, 2018.

56. Ganguly S., Sarkar D. & Ghosh J. J. (1976) Sialic acid and sialidase activity in human endometrial tissue, uterine fluid and plasma under different conditions of uterine dysfunction. *Acta Endocrinol (Copenh)*, 81, 574.

57. Nelson J. D., Jato-Rodriguez J. J., Labrie F. & Mookerjea S. (1977) Glycosyltransferase and UDP-galactose pyrophosphatase activities in the endometrium during oestrous cycle of the rat. *J Endocrinol*, 7.3, 53.

58. Zhu Z., Deng H., Fenderson B. A., Nudelman E. D. & Tsui Z. (1990) Glycosphingolipids of human myometrium and endometrium and their changes during the menstrual cycle, pregnancy and ageing. *J Reprod Fertil*, 88, 71.

59. Takamatsu K., Kamei K., Kubushiro K., Kiguchi K., Nozawa S. & Iwamori M. (1993) Luteal phase-characteristic induction of I3SO3-GalCer in human cervical epithelia and uterine endometria, and follicular phase-characteristic formation of a ganglioside-derived negative charge gradient in different regions of fallopian tubes. *Biochim Biophys Acta*, 1170, 232.

60. Ravn V. & Jensen H. (1988) Thomsen-Friedenreich-related antigen in human endometrium. An immunohistochemical study employing the monoclonal antibody 49H.8. A preliminary report. *Apmis*, 96, 552.

61. Ravn V., Teglbjaerg C. S., Mandel U. & Dabelsteen E. (1992) The distribution of type-2 chain histo-blood group antigens in normal cycling human endometrium. *Cell Tissue Res*, 270, 425.

62. Cramer D. W., Hornstein M. D., Ng W. G. & Barbieri R. L. (1996) Endometriosis associated with the N314D mutation of galactose-l-phosphate uridyl transferase (GALT). *Mol Hum Reprod*, 2, 149.

63. To W. Y., Leung J. C. & Lai K. N. (1995) Identification and characterization of human serum alpha2-HS glycoprotein as a jacalin-bound protein. *Biochim Biophys Acta*, 1249, 58.

64. Kijimoto-Ochiai S. & Uede T. (1995) CD23 molecule acts as a galactose-binding lectin in the cell aggregation of EBV-transformed human B-cell lines. *Glycobiology*, 5, 443.

65. Kijimoto-Ochiai S., Horimoto E. & Uede T. (1994) Demonstration of the interaction between the CD23 molecule and the galactose residue of glycoproteins. *Immunology Letters*, 40, 49.

66. Sakai H., Yamagishi F., Miura M., Hata K., Koyama I., Sakagishi Y. & Komoda T. (1994) Sugar chain heterogeneity of human urinary chorionic gonadotropin determined by serial lectin affinity chromatography: difference between benign and malignant disease. *Tumour Biol*, 15, 230.

What is claimed is:

1. A method for diagnosing endometriosis in a patient, said method comprising:
   (a) obtaining an antibody-containing tissue or an antibody-containing fluid sample from said patient,
   (b) incubating an antigen with said sample, wherein said antigen comprises a Galβ1-3GalNAc disaccharide moiety,
   (c) detecting autoantibody reactivity of said sample to said antigen, and;
   (d) correlating an increased level of autoantibody reactivity with a normal level to diagnose endometriosis in said patient.

2. A method for diagnosing endometriosis in a patient, said method comprising:
   (a) immobilizing an antigen on a solid support, wherein said antigen comprises a Galβ1-3GalNAc disaccharide moiety,
   (b) adding an aliquot of an antibody-containing fluid from a patient to said antigen to form a mixture and incubating the mixture, wherein said antibody binds to said antigen to form a complex, (c) adding anti-human immunoglobulins that are capable of detectably binding to said complex, wherein said anti-human immunoglobulins have a detectable label.

(d) separating free anti-human immunoglobulins from bound anti-human immunoglobulins, (e) measuring the amount of bound anti-human immunoglobulins; and (f) correlating an increased amount of bound anti-human immunoglobulins with a normal amount of bound anti-human immunoglobulins to diagnose endometriosis in said patient.

3. A method for diagnosing endometriosis in a patient, said method comprising:

(a) bringing together in an aqueous medium: (1) a predetermined amount of an antibody to an antigen comprising the Galβ1-3GalNAc disaccharide moiety, wherein said antibody has a detectable label, (2) an antigen which comprises a Galβ1-3GalNAc disaccharide moiety, and (3) an antibody-containing fluid sample from said patient, (b) separating labeled antibodies that are bound to said antigen from antibodies that are not bound to said antigen, (c) measuring the amount of labeled antibodies that are bound to said antigen, and;

(d) correlating a decreased amount of labeled antibodies that are bound to said antigen with a normal amount of labeled antibodies that are bound to said antigen to diagnose endometriosis in said patient.

4. A method for diagnosing endometriosis in a patient, said method comprising:

(a) preparing a reaction mixture by incubating a first antibody which is bound to an antigen with an antibody-containing fluid sample from a patient, wherein said antigen comprises a Galβ1-3GalNAc disaccharide moiety, (b) adding a predetermined amount of a second antibody to the reaction mixture wherein said second antibody recognizes the first antibody and wherein the second antibody has a detectable label, (c) separating free molecules of the second antibody from bound molecules of the second antibody, (d) measuring the signal generated by the bound molecules of the second antibody in the reaction mixture, and;

(e) correlating a decreased level of signal with a normal level of signal to diagnose endometriosis in the patient.

5. The method of claim 4 wherein the anti-human immunoglobulin is enzyme-labeled, said method comprising the additional steps of adding a substrate to the solid support which reacts with the enzyme-labeled anti-human immunoglobulin and incubating, wherein said additional steps are performed between steps (d) and (e).

6. The method of claim 3 wherein the anti-human immunoglobulin is enzyme-labeled, said method comprising the additional steps of adding a substrate to the solid support which reacts with the enzyme-labeled anti-human immunoglobulin and incubating, wherein said additional steps are performed between steps (b) and (c).

7. The method of claim 4 wherein the second antibody is enzyme-labeled, said method comprising the additional steps of adding a substrate to the solid support which reacts with the enzyme-labeled second antibody and incubating, wherein said additional steps are performed between steps (c) and (d).

8. The method of any of claims 2, 3, or 4 wherein said detectable label is selected from the group consisting of dyes, fluorescers, radiolabels, enzymes, chemiluminescers and photosensitizers.

9. The method of any of claims 2, 3, or 4 wherein said detectable label comprises biotin.

10. The method of claim 1, wherein said Galβ1-3GalNAc disaccharide moiety is sialylated.

11. The method of claim 1 wherein said antibody-containing tissue comprises endometrial tissue.

12. The method of claim 1 wherein said antibody-containing fluid is selected from the group consisting of blood, serum, plasma, saliva, tears, sweat, peritoneal fluid, and vaginal secretions.

13. The method of claim 11, wherein the autoantibody reactivity is determined by immunohistochemistry or Western Blot.

14. The method of claim 12, wherein the autoantibody reactivity is determined by Flow Cytometry or Western Blot.

15. The method of any one of claims 1, 11 or 12 wherein the autoantibody reactivity is determined by immunoassay.

16. The method of claim 15 wherein the immunoassay is an immunometric assay.

17. The method of claim 15 wherein the immunoassay is a competitive immunoassay.

18. The method of claim 15 wherein the immunoassay is a competitive immunometric assay.

* * * * *

UNITED STATES PATENT AND TRADEMARK OFFICE
CERTIFICATE OF CORRECTION

PATENT NO. : 6,645,725 B2
DATED : November 11, 2003
INVENTOR(S) : Grant R. Yeaman It is certified that error appears in the above-identified patent and that said Letters Patent is hereby corrected as shown below:

<u>Column 1,</u>
Line 4, insert the following: -- This invention was made with Government support under CA-36432 awarded by the National Institutes of Health. The Government has certain rights in the invention. --

Signed and Sealed this

Twenty-ninth Day of June, 2004

JON W. DUDAS
*Acting Director of the United States Patent and Trademark Office*